United States Patent [19]

Nichols

[11] Patent Number: 4,638,286
[45] Date of Patent: Jan. 20, 1987

[54] REACTIVE GAS SENSOR

[75] Inventor: Leo F. Nichols, Omaha, Nebr.

[73] Assignee: Enron Corp., Houston, Tex.

[21] Appl. No.: 716,183

[22] Filed: Mar. 26, 1985

[51] Int. Cl.$^4$ .......................... H01L 7/00; H01B 1/00
[52] U.S. Cl. ...................................... 338/34; 252/500;
252/512; 252/518; 73/27 R; 428/515; 428/516; 428/518
[58] Field of Search ......................... 252/512, 500, 518; 338/34; 422/88, 90, 98; 73/27 R, 26; 428/515, 518, 516

[56] References Cited

U.S. PATENT DOCUMENTS

| | | |
|---|---|---|
| 4,045,764 | 8/1977 | Ochinose et al. ................. 338/34 |
| 4,269,738 | 5/1981 | Pez ................................. 252/500 |
| 4,347,495 | 8/1982 | Hunter et al. .................... 338/34 |
| 4,394,304 | 7/1983 | Wnek ............................... 252/500 |
| 4,440,669 | 4/1984 | Ivory et al. ....................... 252/500 |
| 4,481,312 | 11/1984 | Hocher ............................ 525/202 |
| 4,510,075 | 4/1985 | Lee et al. ......................... 252/500 |
| 4,510,076 | 4/1985 | Lee et al. ......................... 252/500 |
| 4,608,549 | 8/1986 | Furuy .............................. 252/518 |

FOREIGN PATENT DOCUMENTS 2502401 9/1982 France.

OTHER PUBLICATIONS

*Synthetic Metals*, 4-84, pp. 131-141 "Review of the Synthesis of Polyacetylene and its Stab. to Ambient Atmosphere".
*Synthetic Metals*, 8-84, pp. 475-487 "Microwave Measurement of the Stability of Polyacetylene After Encapsulation".

*Primary Examiner*—Josephine L. Barr
*Attorney, Agent, or Firm*—Donald F. Haas

[57] ABSTRACT

A reactive gas sensor which utilizes an electrically conductive polymer composite which comprises an inner layer of an electrically conductive polymer, intermediate layers of a polymer which exhibits a low degree of gas permeability, and protective outer layers of a polymer which exhibits a low degree of moisture permeability. The preferred polymers for the intermediate layers are ethylene vinyl alcohol copolymers and polyvinylidene chloride. The sensor also includes means for measuring the resistance of the electrically conductive polymer.

8 Claims, No Drawings

REACTIVE GAS SENSOR

BACKGROUND OF THE INVENTION

This invention relates to the use of electrically conductive polymers in sensors for reactive gases and more specifically to the use of composites made of such polymers in such sensors.

Ever since the relatively recent discovery that certain polymers either had or could be made to acquire a high electrical conductivity, there has been much interest in commercial development of such polymers. These electrically conductive polymers could serve as substitutes for metals in a variety of applications requiring high electrical conductivity. Work has been done to develop the use of electrically conductive polymers in batteries, solar cells, semiconductors, electromagnetic shielding, and traditional wiring.

Extensive work has been conducted with a number of polymers including poly(phenylene), poly(phenylene sulfide), poly(phenylene oxide) and polyacetylene. Of the polymers which have been investigated, polyacetylene has shown the most promise up to the present time. Such polyacetylene is usually doped with suitable impurities such as iodine, $AsF_5$ or $HSO_3F$, $SO_3$, sodium, potassium and lithium to increase the conductivity. Such methods are discussed in U.S. Pat. No. 4,269,738 which was issued on May 26, 1981 to Pez and Anderson.

Many polymers are susceptible to degradation or disruption in the presence of air, moisture, and other agents, including ammonia, hydrogen sulfide, methane, chlorine and carbon monoxide. Polyacetylene and several other electrically conductive polymers are no exception. The reactivity of these polymers leads to their instability and thus has created a need for methods or additives to decrease this tendency to be unstable. A variety of methods have been tried including chemical doping, ionic implantation, antioxidizing agents, and blending with a protecting polymer. The present invention uses the instability of such polymers to provide a reactive gas sensor.

SUMMARY OF THE INVENTION

The present invention relates to a reactive gas sensor utilizing an electrically conductive polymer composite which is protected against degradation by oxygen, moisture and other degrading agents including ammonia and carbon monoxide. The composite is comprised of an inner layer of an electrically conductive polymer, intermediate layers of a polymer which exhibits a low degree of reactive gas permeability, and protective outer layers of a polymer which exhibits a low degree of moisture permeability. Ethylene vinyl alcohol copolymers, polyvinylidene chloride, and polyethylene terephthalate, polyformaldehyde and polyvinyl fluoride are suitable materials for the gas barrier layer. The outer layer may be of any relatively moisture impermeable polymer including low density polyethylene, polypropylene and polytetrafluoroethylene. The electrically conductive polymer is preferably doped polyacetylene but can be any of the known electrically conductive polymers including poly(phenylene), poly(phenylene sulfide) and poly(phenylene oxide). Finally, the sensor of the present invention includes means for measuring the resistance of the electrically conductive polymer in the composite to be able to determine when a reactive gas has permeated to the electrically conductive polymer.

DETAILED DESCRIPTION OF THE INVENTION

Although they are relatively new, electrically conductive polymers and their methods of manufacture are well known. They are discussed in U.S. Pat. No. 4,269,738, discussed above and also in U.S. Pat. No. 4,394,304 issued July 19, 1983 to Wnek. Also, "Review of the Synthesis of Polyacetylene and its Stabilization to Ambient Atmosphere" by Mahmoud Aldissi published in April of 1984 in *Synthetic Metals*, Volume 9, contains a detailed description of the polymerization reaction of acetylene and the formation of polyacetylene electrically conductive polymers. Other methods of manufacture are disclosed in U.S. Pat. Nos. 4,108,942, 4,093,790, 4,228,060, 4,222,903, 4,204,216 and 4,200,716.

Polyvinylidene chloride, ethylene vinyl alcohol copolymers, polyethylene terephthalate, polyformaldehyde and polyvinyl fluoride are well known as gas barrier materials for use in food packaging films. Consequently, the methods of manufacture of these materials are well known. For example, U.S. Pat. No. 3,560,461 issued Feb. 2, 1971 to Yonezu, Nishoka and Mukumoto discloses a method for making ethylene vinyl alcohol copolymers by saponifying ethylene vinyl acetate copolymers. In such ethylene vinyl alcohol copolymers, the oxygen permeability generally improves as the degree of saponification increases and it is preferred that the degree of saponification be greater than 96%.

The methods of manufacture of the polymers for the protective outer layer are also well known. Low density polyethylene, for instance, is a polymer which has been manufactured for many years and its methods of manufacture are described in literally thousands of patents and articles. The type of low density polyethylene which is preferred for use in the present invention is that type of low density polyethylene which is commonly used in wire and cable applications.

The composite of the present invention can be manufactured by a variety of methods, depending upon the desired form for the composite. The different layers can be formed separately and laminated together. They also can be coextruded into an integral article of manufacture. The individual layers of the moisture barrier and gas barrier can be adhered to the exposed surfaces of the conductive layer with a modified olefin polymer. A uniform layering can be obtained by heat rolling the article of manufacture. The moisture barrier will be the most external layer to further protect the gas barrier from moisture hydrolysis. The composite may be in the form of a wire or cable wherein the electrically conductive layer is totally within the other layers. It may also be manufactured as a flat sheet.

The sensor of the present invention utilizes the composite described above. In order to complete the sensor, the composite must be connected to means for measuring the resistance of the electrically conductive polymer. When the resistance of the electrically conductive polymer greatly increases, then it is known that a reactive gas has permeated through the barrier layers to the electrically conductive polymer. There are any number of means in which the resistance of the electrically conductive polymer can be measured. The composite can be connected to a voltage ohmmeter which will directly measure the resistance. Another alternative would be to connect the composite to a simple system including a separate power source and a light bulb. When the light goes out, it is obvious that the resistance of the electrically conductive polymer has increased to infinity because a reactive gas has permeated thereto. This invention contemplates a system wherein the reactive gas is removed and the composite becomes electrically conductive again.

As shown in the following examples, the design of the composite is varied to increase or decrease the life of the sensor. Specifically, the thicknesses of the layers of a polymer having a low degree of gas permeability are varied. As the thickness of the gas barrier is increased, the lifetime of the sensor increases. The lifetime of a sensor generally increases in accordance with the square of the thickness of the barrier layer.

The sensor of the present invention can be used in a variety of applications. One such application is in the storage of blood plasma which is sensitive to oxygen but can be stored over a relatively long period of time. The sensor is placed in the blood plasma and indicates if there has been an oxygen leak into the container. The sensor of the present invention is also useful in the storage and handling of other oxygen sensitive materials such as titanium trichloride, a commonly used catalyst component which is extremely sensitive to the presence of oxygen. The sensor can also be used in the monomer feed to chemical reactors where oxygen is undesirable. One example of this is the propylene in the production of polypropylene. The sensor could also be used to detect long-term oxygen exposure in vapor head of cooling towers. The combination of long-term oxygen exposure and water exposure oftens causes corrosion and scale in such towers. The sensor of the present invention could also be used to detect the presence of conditions which encourage corrosion and scale production.

EXAMPLE

A 0.01 inch thick electrically conducting polymer blend of doped polyacetylene is prepared following the techniques described by Wnek in U.S. Pat. No. 4,394,304 and is used to make three composite structures according to the present invention. The resulting composite structures have a conduction of approximately 5 mho/cm. The top and bottom surfaces are coated with a thin layer, 0.00001 inches thick, of a modified olefin polymer adhesive. These surfaces are laminated with a commercial oxygen and moisture barrier plastic film consisting of a 0.064 inch film of ethylene vinyl alcohol copolymer and a 0.001 inch thick film of low density polyethylene. The ethylene vinyl alcohol copolymer surface of the barrier film is attached to the adhesive. The resulting laminants are heat rolled at approximately 180° F. to form a sealed gas and moisture tight shield for the conducting polymer blend.

Voltage ohmmeters are connected to the composite structures to measure the resistance thereof. The composites are then stored and monitored to determine the length of time before oxygen permeates to the electrically conductive polymer, causing it to degrade and greatly increase its resistance. The following table shows the length of time it takes before each of the composites fails. It can be seen that the time for failure increases as the thickness of the gas barrier increases.

TABLE

| Thickness of Gas Barrier Layer | Time for Sensor Failure |
| --- | --- |
| 0 inches | 2 weeks |
| 0.026 inches | 2 months |
| 0.045 inches | 6 months |
| 0.064 inches | 1 year |

I claim:
1. A reactive gas sensor which comprises:
   (a) an electrically conductive polymer composite comprising:
      (i) an inner layer of an electrically conductive polymer selected from the group consisting of polyacetylene, poly(phenylene), poly(phenylene sulfide) and poly(phenylene oxide),
      (ii) intermediate layers of a polymer which exhibits a low degree of gas permeability, and
      (iii) protective outer layers of a polymer which exhibits a low degree of moisture permeability, and
   (b) means for measuring the resistance of the electrically conductive polymer.
2. The sensor of claim 1 wherein the polymer which forms the intermediate layers is selected from the group consisting of ethylene vinyl alcohol copolymers, polyvinylidene chloride, polyethylene terephthalate, polyformaldehyde and polyvinyl fluoride.
3. The sensor of claim 2 wherein the electrically conducting polymer is polyacetylene.
4. The sensor of claim 2 wherein the polymer which forms the protective outer layers is selected from the group consisting of low density polyethylene, polypropylene and polytetrafluoroethylene.
5. An electrically conductive polymer composite which comprises:
   (a) an inner layer of an electrically conductive polymer selected from the group consisting of polyacetylene, poly(phenylene), poly(phenylene sulfide) and poly(phenylene oxide),
   (b) intermediate layers of a polymer which exhibits a low degree of gas permeability, and
   (c) protective outer layers of a polymer which exhibits a low degree of moisture permeability.
6. The composite of claim 5 wherein the polymer which forms the intermediate layers is selected from the group consisting of ethylene vinyl alcohol copolymers, polyvinylidene chloride, polyethylene terephthalate, polyformaldehyde and polyvinyl fluoride.
7. The composite of claim 6 wherein the electrically conducting polymer is polyacetylene.
8. The composite of claim 6 wherein the polymer which forms the protective outer layers is selected from the group consisting of low density polyethylene, polypropylene and polytetrafluoroethylene.

* * * * *